United States Patent [19]

Stout et al.

[11] Patent Number: 5,577,515
[45] Date of Patent: Nov. 26, 1996

[54] APPLICATOR ASSEMBLY FOR APPLYING PROTECTIVE SHEATHS TO MEDICAL PATIENT RESTRAINING BELTS AND METHOD

[76] Inventors: Richard R. Stout, 27474 SW. Mountain Rd., West Linn, Oreg. 97068; Gregory E. Skipper, 20600 NE. Kingsgrade Rd., Newberg, Oreg. 97132

[21] Appl. No.: 523,786

[22] Filed: Sep. 5, 1995

[51] Int. Cl.⁶ .................................................. A61F 5/37
[52] U.S. Cl. ........................................ 128/846; 128/876
[58] Field of Search ................................. 128/845, 846, 128/849–856, 842, 844, 918, 869–876

[56] References Cited

U.S. PATENT DOCUMENTS

| | | |
|---|---|---|
| 620,356 | 2/1899 | Pratt . |
| 2,333,346 | 11/1943 | Sweetland ........................ 128/876 |
| 3,228,555 | 10/1963 | Pinto ................................. 221/199 |
| 4,009,494 | 3/1977 | Nusbaum .......................... 128/876 |
| 4,177,807 | 12/1979 | Ocel et al. ........................ 128/133 |
| 4,517,860 | 5/1985 | Dameron, Jr. ..................... 81/487 |
| 4,569,095 | 2/1986 | Holling ............................. 128/876 |
| 4,911,106 | 3/1990 | Goodwin .......................... 128/870 |
| 5,197,176 | 3/1993 | Reese ............................... 29/278 |

Primary Examiner—Michael A. Brown
Attorney, Agent, or Firm—Eugene D. Farley

[57] ABSTRACT

A protective sheath applicator assembly for encasing medical patient retaining belts, thereby protecting them from fouling by patient bodily emissions. The assembly includes a longitudinally collapsible tubular sheath and sheath applicator having a central segment for mounting a quantity of sheath material, a first end segment for connection to one of the belt components to enable transfer of the sheath from the applicator to the belt component, and a restraining segment for preventing the sheath from working endwise off the bar. In use, the bar is clipped to one of the restraining belt components and the sheath transferred thereto by sliding it endwise. The bar then is disconnected, and the companion seat belt component clipped to the first seat belt component. The patient then is introduced and the seat belts fastened endwise together in the usual manner. Thereafter the collapsed sheath is extended to cover the second restraining belt component so that the belt is covered and protected along its entire length.

8 Claims, 2 Drawing Sheets

U.S. Patent    Nov. 26, 1996    Sheet 1 of 2    5,577,515
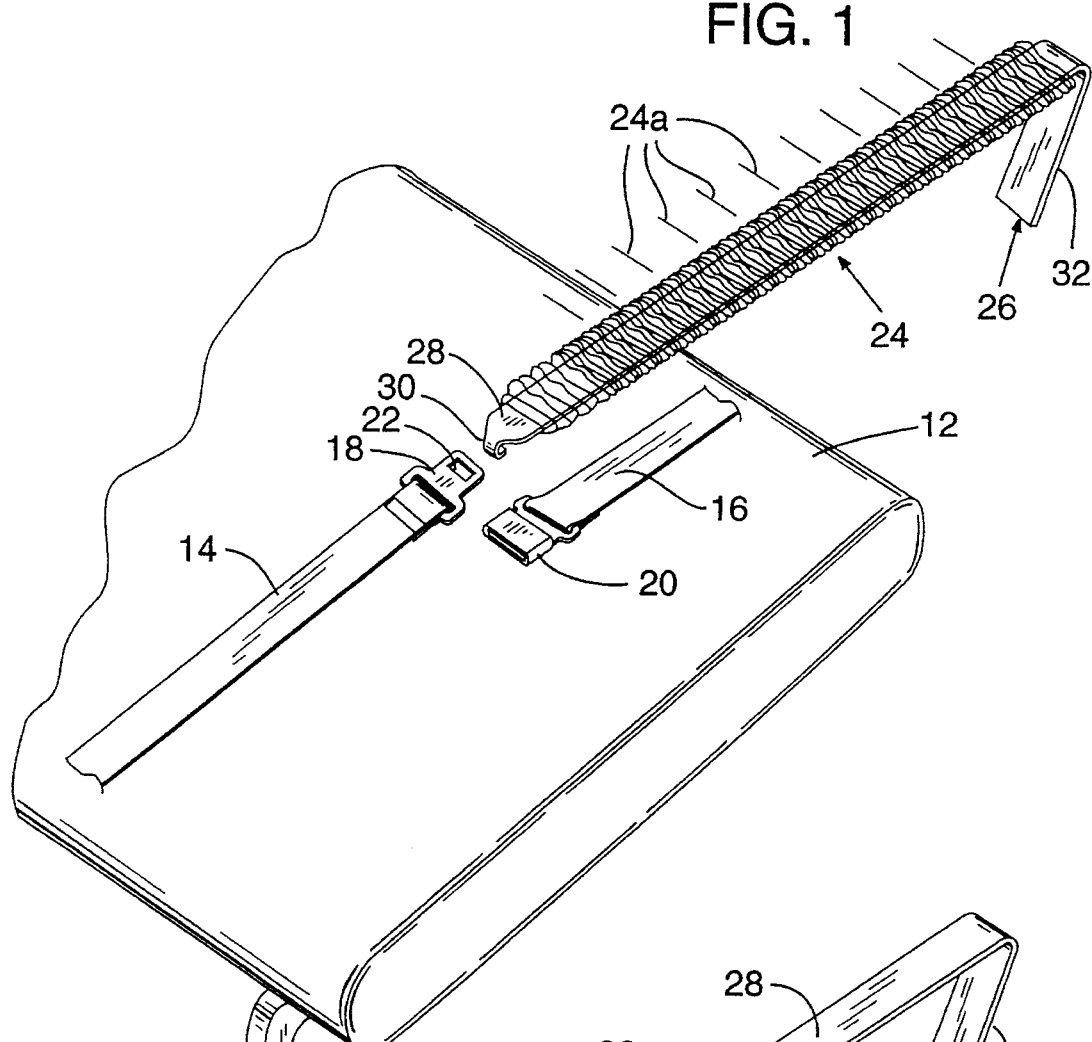
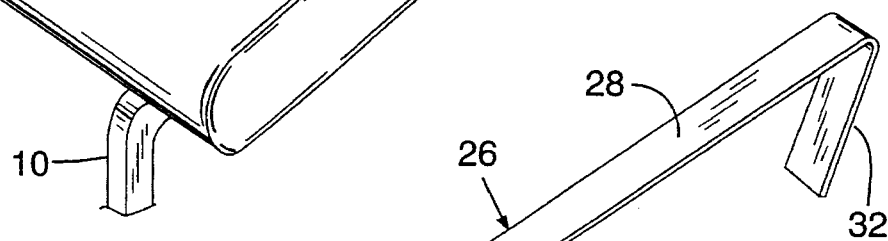
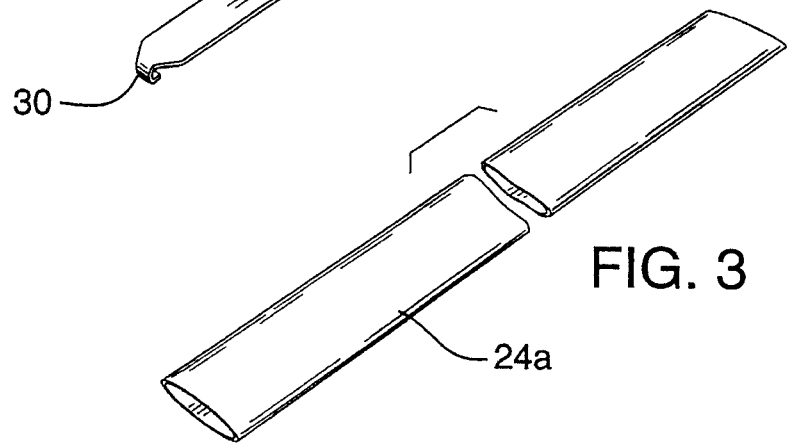

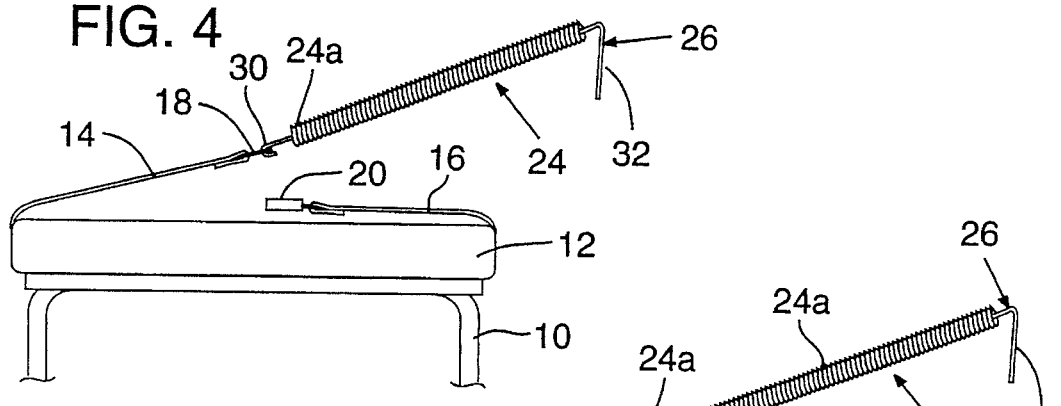
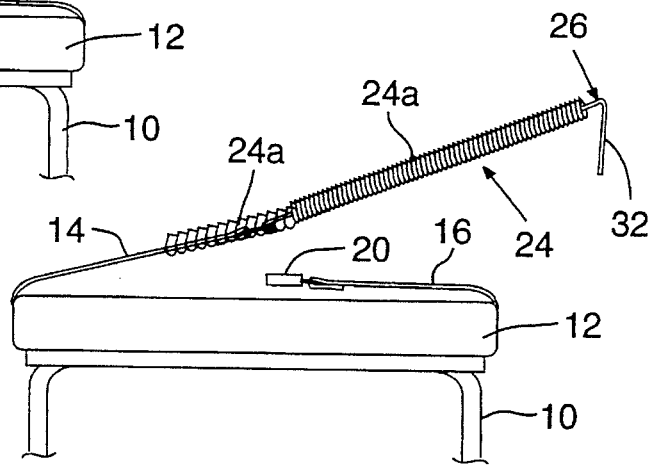
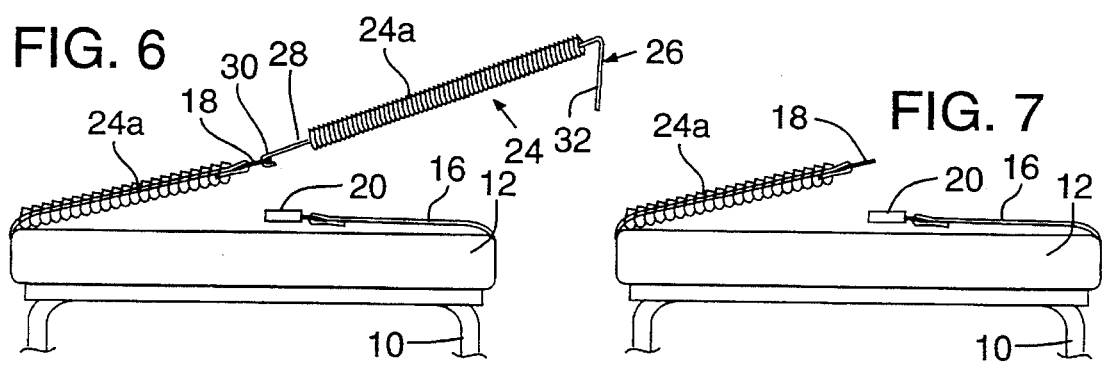
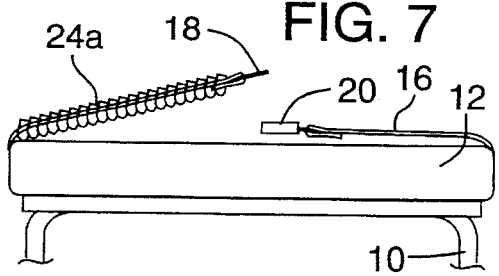
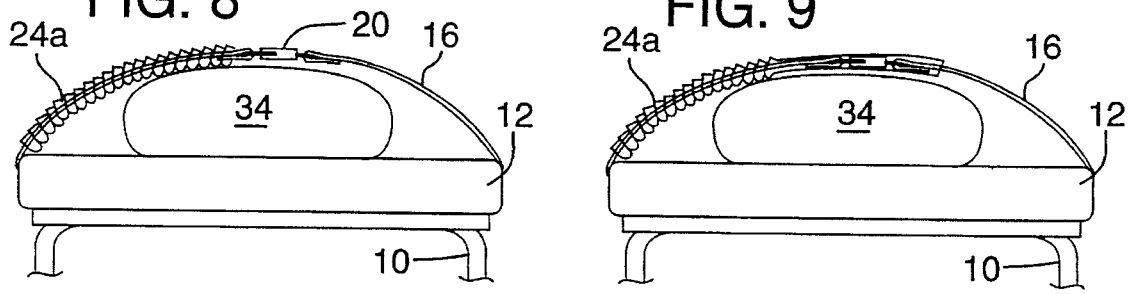
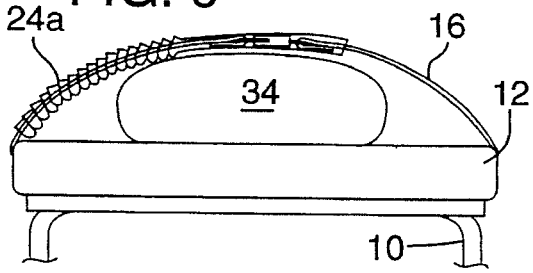
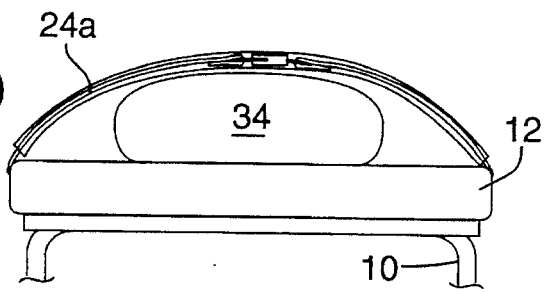

APPLICATOR ASSEMBLY FOR APPLYING PROTECTIVE SHEATHS TO MEDICAL PATIENT RESTRAINING BELTS AND METHOD

BACKGROUND OF THE INVENTION

1. Field of the Invention

This invention relates to an assembly for applying protective sheaths to the restraining belts used in medical patient management in conjunction with ambulance cots, stretchers, medical emergency beds, wheelchairs and the like.

2. Description of the Prior Art

When a medical patient is placed on an ambulance stretcher or hospital emergency room cot he often is strapped on with one or more restraining belts. These resemble automobile safety belts. They comprise at least two components, each anchored at one end to a frame member and provided at its free end with a clip for adjustable, releasable, interengagement with its companion component.

In use, the belts often become fouled with blood, vomit, and other body fluids. Contamination of equipment and potential cross contamination of patients is of serious concern. Accordingly it becomes necessary to wash the belts at frequent intervals with disinfectant solutions such as Chlorox. These solutions often are so strong that the belts soon disintegrate and have to be replaced. Since the belts are expensive, their replacement introduces into the patient care program an undesirable element of cost.

It would be desirable to protect the belts with a removable, disposable sheath of inexpensive commercial plastic tubing. However, mounting the tubing on the belt components is a tedious and time consuming procedure. It is the general purpose of the present invention to provide a sheath applicator assembly which is adaptable for use with conventional safety belts; which is easy and safe to use and of low cost; which has a large sheath storage capacity; and which can be hung up out of the way when not in use.

SUMMARY OF THE INVENTION

The sheath applicator assembly of our invention is adapted for use with a medical patient restraining belt comprising first and second belt components having free ends adapted to be releasably interconnected by clip fasteners or other suitable interconnecting means. The assembly basically comprises a longitudinally collapsible tubular sheath, such as a length of commercial plastic tubing, and an applicator for mounting the sheath on the belt components.

The applicator comprises an elongated bar having a central segment and first and second end segments.

The central segment is contoured and dimensioned to support a plurality of sheath units, in longitudinally collapsed, accordion-pleated condition.

The first bar end segment includes attaching means for releasable attachment to one of the belt components. This permits releasable coupling of the first bar segment to the belt component in end to end relation. The second bar end segment, which may comprise a length of the bar bent at an acute angle, provides a retainer for retaining the sheath on the applicator in its collapsed condition during use and storage.

The applicator is used by first mounting the sheath units on the applicator in longitudinally collapsed condition. The applicator then is coupled end to end with one of the belt components. One of the sheath units in its collapsed condition then is transferred from the applicator to the first belt component, after which the applicator is disconnected.

Thereafter, the first belt component is coupled to the second belt component, and the collapsed sheath extended to substantially its full length, thereby transferring it in part to the second belt component and covering the entire belt.

THE DRAWINGS

In the drawings:

FIG. 1 is a fragmentary view illustrating the construction and manner of use of the herein described sheath applicator assembly.

FIG. 2 is a top perspective view of the applicator.

FIG. 3 is a foreshortened top perspective view of a length of sheath material which is used in conjunction with the applicator of FIG. 2.

FIGS. 4–10 inclusive are views in end elevation illustrating in progressive sequence the manner of use of the herein described sheath applicator assembly.

DESCRIPTION OF A PREFERRED EMBODIMENT OF THE INVENTION

As illustrated in the drawings, the presently described protective sheath applicator assembly is designed for use in conjunction with such medical patient supporting structures as ambulance cots or hospital emergency beds including a frame 10 which supports a mattress 12. The beds are provided with one or more patient-restraining belts. These resemble ordinary automobile safety belts and include a first belt component 14 and a cooperating second belt component 16.

One of the ends of each belt component is anchored to frame 10, as illustrated. The free ends of the belts are provided with interconnecting means for releasable interconnection of the belt components during use.

Although Velcro or other types of fasteners may be used for this purpose, in the usual belt assembly clip connectors are employed.

As shown in FIG. 1, such connectors include a male clip component 18 and a female clip component 20. The male clip component is formed with an eye or opening 22.

The sheath applicator assembly used for mounting a protective sheath on the two belt components comprises broadly a bar-type applicator having mounted thereon one or a plurality of sheaths in longitudinally collapsed condition.

The sheath component of the assembly, indicated generally at 24, broadly comprises a single length of sheath material; a single length containing transverse tear perforations to define individual sheath units 24a; or individual sheaths cut to length and arranged end to end on the applicator in longitudinally collapsed, accordion-pleated condition. If desired, the sheath may be imprinted with desired merchandising information.

In its extended condition, each sheath unit 24a has the appearance illustrated in FIG. 3. It is cut to length to suit the size of the seat belt components which it is to encase, for example to a length of about four feet.

The sheath may be variously constituted. However, it is contemplated that commercial plastic tubing such as polyethylene tubing of appropriate diameter will be used.

The applicator member of the assembly, FIG. 2, comprises an elongated bar of suitable length and material. It preferably is flat, although a bar of round or oval cross section may be employed, if desired.

Applicator 26 has a central section 28 which is contoured and dimensioned to support sheath 24 in collapsed condition, as illustrated in FIG. 1. Its cross section should be such as to permit easy relative motion of sheath and bar so that the sheath may be easily applied and removed.

Applicator 26 also is provided with a first end segment having means for attachment to one of the restraining belt components. Although various interconnecting members may be employed, it is preferred to use the illustrated hook and eye connector. In this case, the first end segment of the bar is contoured in the shape of a hook 30 dimensioned for releasable insertion in eye 22 of male clip component 18.

The other end segment of applicator bar 26 serves triple purposes. First, it serves as a retainer for retaining sheath 24 on the central segment of the bar. Since the sheath is in the compressed condition, it tends to move lengthwise during storage and, if unrestrained, will slide off the end of the bar unless restraint is provided.

The second function is that of providing a hook for hanging the assembly in a suitable location, convenient to the hand of the operator.

The third function is that of providing a buttress for pressing the applicator against the chest or abdomen of the operator as he threads the sheath material on the bar when loading it in the first instance.

A preferred member for achieving these three functions is segment 32 of the bar reversely bent at an acute angle relative to the central segment 28 thereof. A preferred angle for the intended purpose is an angle of from 30°–90°. When this is the case, the sheath is restrained from working its way off the applicator. Also, a hook is provided for hanging the applicator and its sheath load on any suitable support, such as a coat hanger, nail, or peg. Still further, particularly if the bar is a flat bar, a buttress or abutment is provided for assistance in threading the sheath on the central segment of the bar.

In use, after loading the sheath on the applicator, hook 30 is interengaged with eye 22 and the two members arranged end to end, FIG. 4. A sufficient amount of the sheath, for example four feet, is transferred to completely encase both components 14, 16 of the belt. If the tubing has been perforated, it is torn at the perforations. If it is entire, it may be cut transversely to length. Preferably, it has been precut to length to provide sheath units 24a so that no further action is needed.

The applicator assembly next is disengaged as shown in FIG. 7. After a patient 34 has been placed on the cot, the ends of the belt components are clipped together in the usual manner, FIG. 8. It then is a simple matter to slide the sheath endwise to its extended position in which it encases not only seat belt component 14 but also the companion seat belt component 16. After use, it is removed and discarded and another sheath length applied.

This sequence is illustrated in detail in FIGS. 4–10 of the drawings.

FIG. 4 illustrates the first step of the operation with belt components 14 and 16 separated and with applicator 26, fully loaded with a supply of sheaths 24a, coupled to the end of belt component 14.

FIG. 5 shows the same situation, with the terminal one of sheaths 24a partly loaded onto belt component 14.

FIG. 6 is similar, but illustrates the sheath 24a fully loaded onto component 14.

FIG. 7 illustrates the next step in the operation, the removal of applicator 26. The hospital or ambulance cot now is ready for the reception of patient 34.

FIG. 8 illustrates the patient on the cot with the meeting ends of belt components 14, 16 coupled together. Sheath 24a still is mounted exclusively on belt component 14.

FIG. 9 shows sheath 24a partly threaded on the companion belt component 16.

FIG. 10 illustrates the working position of the sheath, fully extended and completely covering both of belt components 14 and 16 in which position it protects the entire length of the belt assembly from soiling and contamination.

Having thus described in detail a preferred embodiment of the present invention, it will be apparent to those skilled in the art that many physical changes may be made without altering the inventive concepts and principles embodied therein. The present embodiments therefore are to be considered in all respects as illustrative and not restrictive, the scope of the invention being indicated by the appended claims.

We claim:

1. For use with a medical patient restraining belt comprising first and second belt components having free ends and interconnecting means on the free end of each component for releasably interconnecting the same during use, a protective sheath applicator assembly comprising in combination:

a) a longitudinally collapsible tubular sheath, and b) a sheath applicator for mounting the sheath on the first belt component and comprising an elongated bar having a central segment and first and second end segments, c) the central segment being contoured and dimensioned to support the sheath in a longitudinally collapsed condition, d) the first bar end segment including attaching means for releasable attachment to one of the belt component interconnecting means to permit releasable coupling of the first bar segment to the said belt component in end to end relation, thereby enabling transferring the sheath from the bar to the belt component.

2. The applicator of claim 1 wherein the said second end segment of the bar includes sheath retaining means for retaining the sheath on the bar in its longitudinally collapsed condition.

3. The applicator assembly of claim 2 wherein the sheath retaining means comprises the said second end segment bent at an acute angle with respect to the bar central segment.

4. The sheath applicator assembly of claim 3 wherein the angle is from 30°–90°.

5. The sheath applicator assembly of claim 1 wherein the interconnecting means on the free ends of the belt components comprises clip-type interconnecting means having interconnecting male and female clip components, and the attaching means on the first bar end segment comprises hook and eye attaching means.

6. The sheath applicator assembly of claim 1 wherein the interconnecting means on the free end of each component for releasably interconnecting the same comprises clip-type interconnecting means including a male member having therein an opening, and wherein the said second end segment of the bar comprises a hook dimensioned and contoured for releasable engagement with the opening.

7. For use with a medical patient restraining belt comprising first and second belt components having free ends and clip type belt component interconnecting means on the free end of each component, the clip component on one of the free ends comprising a male member having an opening therein, a protective sheath applicator assembly comprising in combination:

a) a longitudinally collapsible tubular sheath, and b) a sheath applicator for mounting the sheath on the first belt component and comprising an elongated bar having a central segment and first and second end segments, c) the central segment being contoured and dimensioned to support the sheath in a longitudinally collapsed condition, b) the first bar end segment including a hook for releasable attachment to the opening in the male member of the said belt components for releasable attachment to the said belt component in end to end relation, thereby enabling transferring the sheet from the bar to the belt component e) the second bar end segment comprising a length of the bar bent at an acute angle with reference to the central segment thereof, thereby providing retaining means for retaining the sheath on the bar in its longitudinally collapsed condition.

8. The method of mounting a protective sheath on a medical patient restraining belt comprising first and second belt components comprising mounting the sheath on a bar applicator in longitudinally collapsed condition, a) coupling the applicator end to end with one of the belt components, b) transferring the belt in its collapsed condition from the applicator to the said first belt component, c) disconnecting the applicator from the first belt component, e) coupling the first belt component to the second belt component, and f) extending the collapsed sheath to substantially its full length, thereby transferring it in part to the second component and covering substantially the entire belt.

* * * * *